(12) United States Patent
Seo et al.

(10) Patent No.: US 11,617,885 B2
(45) Date of Patent: Apr. 4, 2023

(54) MOUTHPIECE FOR SKIN TREATMENT AND APPARATUS FOR SKIN TREATMENT USING ELECTRICAL ENERGY

(71) Applicant: JEISYS MEDICAL INC., Seoul (KR)

(72) Inventors: Suk Bae Seo, Seoul (KR); Ja Young Kim, Seoul (KR); Ho Joon Seo, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 37 days.

(21) Appl. No.: 17/064,800

(22) Filed: Oct. 7, 2020

(65) Prior Publication Data

US 2021/0016086 A1 Jan. 21, 2021

Related U.S. Application Data

(63) Continuation of application No. PCT/KR2019/004383, filed on Apr. 11, 2019.

(30) Foreign Application Priority Data

Apr. 12, 2018 (KR) .......................... 10-2018-0042645
Aug. 10, 2018 (KR) .......................... 10-2018-0093822

(51) Int. Cl.
  *A61N 1/00* (2006.01)
  *A61N 1/32* (2006.01)
  *A61N 1/05* (2006.01)

(52) U.S. Cl.
  CPC ........... *A61N 1/328* (2013.01); *A61N 1/0548* (2013.01)

(58) Field of Classification Search
  None
  See application file for complete search history.

(56) References Cited

U.S. PATENT DOCUMENTS

2009/0048647 A1* 2/2009 Tingey ............... A61N 1/36031
  607/62
2011/0022126 A1* 1/2011 Taylor .................. A61N 1/0548
  607/61

(Continued)

FOREIGN PATENT DOCUMENTS

CN 105708543 A * 6/2016
KR 10-0634970 B1 10/2006

(Continued)

OTHER PUBLICATIONS

Office Action issued in KR 10-2018-0042645; mailed by the Korean Intellectual Property Office dated May 28, 2018.

(Continued)

*Primary Examiner* — John R Downey
*Assistant Examiner* — Anant A Gupta
(74) *Attorney, Agent, or Firm* — Studebaker & Brackett PC

(57) ABSTRACT

Provided is a monopolar skin treatment apparatus using electrical energy in a high frequency wavelength band in which a retaining ligament, a blood vessel, and a fibrous tissue of a deep part is utilized as an electricity passage to actively prevent the skin from sagging due to the aging. The mouthpiece for skin treatment includes a frame, and a ground electrode unit on the frame. The frame includes a first frame disposed in front, a second frame extending rearward from one end portion of the first frame, and a third frame extending rearward from an opposite end portion of the first frame. The ground electrode unit is integrally formed with the first frame, the second frame, and the third frame while continuously extending.

7 Claims, 8 Drawing Sheets

(56) References Cited

U.S. PATENT DOCUMENTS

| | | | | |
|---|---|---|---|---|
| 2012/0156648 A1* | 6/2012 | Kaufman | ............. | A61C 19/066 |
| | | | | 433/32 |
| 2016/0038734 A1* | 2/2016 | Nemeh | ................ | A61C 17/005 |
| | | | | 433/32 |
| 2016/0158534 A1* | 6/2016 | Guarraia | ............... | A61N 1/0456 |
| | | | | 607/134 |
| 2019/0029917 A1* | 1/2019 | George | .................. | A61N 1/328 |
| 2020/0179690 A1* | 6/2020 | Schepis | .............. | A61N 1/36192 |
| 2020/0254243 A1* | 8/2020 | Kim | ..................... | A61N 1/0548 |

FOREIGN PATENT DOCUMENTS

| KR | 10-2011-0130788 A | 12/2011 |
|---|---|---|
| KR | 10-1191951 B1 | 10/2012 |
| KR | 10-1656660 B1 | 9/2016 |
| KR | 10-2017-0014482 A | 2/2017 |
| KR | 10-2017-0025060 A | 3/2017 |
| KR | 10-1757593 B1 | 7/2017 |

OTHER PUBLICATIONS

International Search Report issued in PCT/KR2019/004383; dated Jul. 19, 2019.

* cited by examiner

MOUTHPIECE FOR SKIN TREATMENT AND APPARATUS FOR SKIN TREATMENT USING ELECTRICAL ENERGY

CROSS-REFERENCE TO RELATED APPLICATIONS

The present application is a continuation of International Patent Application No. PCT/KR2019/004383 filed on Apr. 11, 2019, which is based upon and claims the benefit of priority to Korean Patent Application Nos. 10-2018-0042645 filed on Apr. 12, 2018, and 10-2018-0093822 filed on Aug. 10, 2018. The disclosures of the above-listed applications are hereby incorporated by reference herein in their entirety.

BACKGROUND

Embodiments of the inventive concept described herein relate to a mouthpiece for skin treatment and an apparatus for skin treatment using electrical energy.

Recently, various skin treatment devices have been developed to remove wrinkles, restore skin elasticity, and remove sebum. A skin, which has no wrinkle, is taut, thick, and dense without sagging, makes a person look younger and have an attractive outer appearance.

Skin treatment devices to apply energy have been provided in various types, such as an HIFU type to transmit a ultrasonic wave to a skin tissue, a type (especially, a higher frequency type, a radio frequency (RF) type) to transmit an electromagnetic wave to a skin tissue, and an optical type to irradiate a laser beam to a skin tissue.

According to the type to transmit the electromagnetic wave to the skin tissue, a singular RF electrode or a plurality of RF electrodes are introduced into a deep part, such that damaged collagen and elastic fibers are removed from the deep part of the skin using the electrical energy, thereby promoting the regeneration of the skin. In addition, skin pigmentation, acne marks and wrinkles are improved.

Meanwhile, the skin treatment device using the electrical energy may use a DC power source and an AC power source depending on the types of power sources, and a scheme of using RF energy, which has a high frequency band, of AC power has been mainly developed. In addition, the skin treatment devices are classified into a bipolar-type device to apply energy a part close to an electrode and a monopolar-type device to transmit energy at a remote place to a skin tissue.

According to the bipolar-type device, electrical energy is transmitted to a shorter distance between a plurality of electrodes, and there is a limitation in that energy is intensively applied to a thin and narrow part.

According to the monopolar-type device, electrical energy is transmitted by using a first electrode unit 1 as a power terminal and a second electrode unit 2 separately provided as a ground terminal (see FIGS. 1A to 1D). Meanwhile, the first electrode unit 1 may include a plurality of needle electrodes to be applied to a dermal layer to transmit electrical energy to the deep part of the skin. However, this is provided for illustrative purpose of the first electrode unit 1, and the form of the first electrode unit 1 is not limited to the form of a plurality of needle electrodes.

Meanwhile, a retaining ligament connects a skin to a bone, and contains a large amount of moisture, such that the retaining ligament may be utilized as an electricity passage. As illustrated in FIG. 3, the retaining ligament is divided into several strands as the central strand of the retaining ligament is split from a bone tissue toward a skin tissue (outer side). When such a support structure is weakened, thinned, and loses elasticity due to aging, a facial part may be aged. Accordingly, to solve the problem, a position, which is close to the skin to make an electricity flow similar to an electricity flow originated from a bone, may be oral mucosa, and FIG. 4 illustrates photographs of a part close to the skin to be used as the ground (see a dotted area of FIG. 4).

Accordingly, when a facial surface of a skin is treated using electrical energy, and when the retaining ligament, or a blood vessel, or a fibrous tissue of the facial surface is utilized as an electricity passage, the aging and the shrinking of the retaining ligament and other structures are recovered, thereby actively preventing the skin from sagging due to the aging.

However, according to the skin treatment device in a typical monopolar type, when the first electrode unit 1 makes contact with a target part, and the second electrode unit 2 makes contact with a specific body part (for example, a back, an abdomen, and a hip, see FIG. 2), the first electrode unit 1 is away from the second electrode unit 2, so electricity mainly flows only in a surface layer of the skin and a retaining ligament, a blood vessel, or a fibrous tissue of the deep part of a facial surface is not utilized as an electricity passage.

SUMMARY

Embodiments of the inventive concept provide an apparatus for skin treatment in a monopolar type using a high frequency wavelength band, capable of actively improving a facial surface sagging as a skin is aged, by using a retaining ligament, a blood vessel, or a fibrous tissue of a deep part as an electricity passage.

The objects of the inventive concept are not limited to the above, but other effects, which are not mentioned, will be apparently understood to those skilled in the art.

According to an exemplary embodiment, a mouthpiece for skin treatment may include a frame, and a ground electrode unit on the frame. The frame may include a first frame disposed in front, a second frame extending rearward from one end portion of the first frame, and a third frame extending rearward from an opposite end portion of the first frame. The ground electrode unit may be integrally formed with the first frame, the second frame, and the third frame while continuously extending.

At least one front tooth may be placed on the first frame, at least one right molar may be placed on the second frame, and at least one left molar may be placed on the third frame, when the frame is inserted into a mouth.

The ground electrode unit may be disposed in at least a portion between a lip and at least one front tooth, at least a portion between a right cheek mucosa and at least one right molar, and a portion between a left cheek mucosa and at least one left molar, when being inserted into a mouth.

The ground electrode unit may electrically interact with an external power electrode unit such that an alternating current (AC) current in a high frequency wavelength band flows.

A front portion of the first frame may have a curvature, and at least a portion of the second frame and the third frame may have a large area part having a height increased toward a rear portion.

At least one of the first frame, the second frame, and the third frame may include a first cover disposed at an outer side, a second cover disposed at an inner side, and a seating part interposed between the first cover and the second cover, and the ground electrode unit may be disposed on at least a portion of an outer side surface of the first cover or constitutes the at least a portion of the outer side surface of the first cover.

The frame may include a non-conductive material, and the ground electrode unit may be disposed on an intermediate portion of the outer side surface of the first cover or may constitute the intermediate portion of the outer side surface of the first cover such that an upper portion and a lower portion of the outer side surface of the first cover are exposed to an outside. The seating part may be stuck between a plurality of upper teeth and a plurality of lower teeth, when the seating part is inserted into the mouth.

The ground electrode unit may cover at least 95% of the outer side surface of the first cover.

An intaglio groove corresponding to a tooth shape of a wearer may be formed in the seating part.

According to an exemplary embodiment, an apparatus for skin treatment may include an electric control unit, a mouthpiece for skin treatment according to one of claim 1 to claim 9, which is electrically connected to the electric control unit, and a handpiece electrically connected to the electric control unit. The handpiece may include a power electrode unit that receives power from the electric control unit and electrically interacts with the ground electrode unit of the mouthpiece for the skin treatment such that an AC current in a high frequency wavelength band flows.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1A:
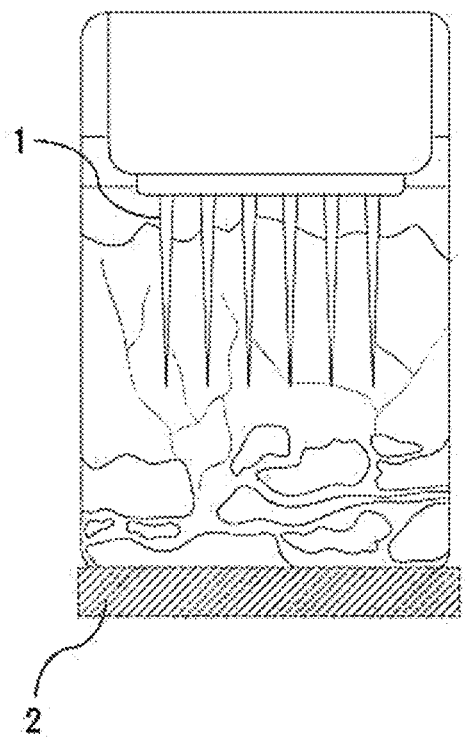
FIGS. 1A to 1D are views conceptually illustrating a treatment process using an RF needle electrode.
Figure 1B:
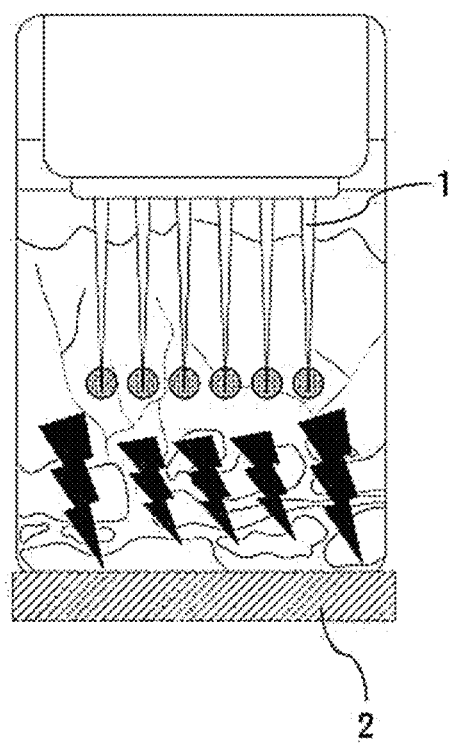
Figure 1C:
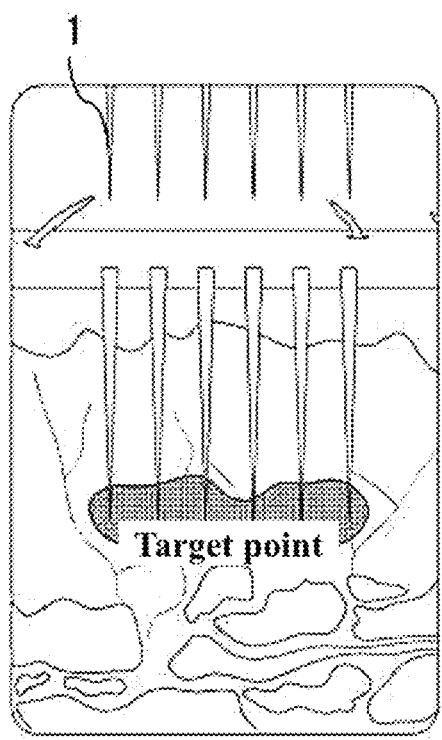
Figure 1D:
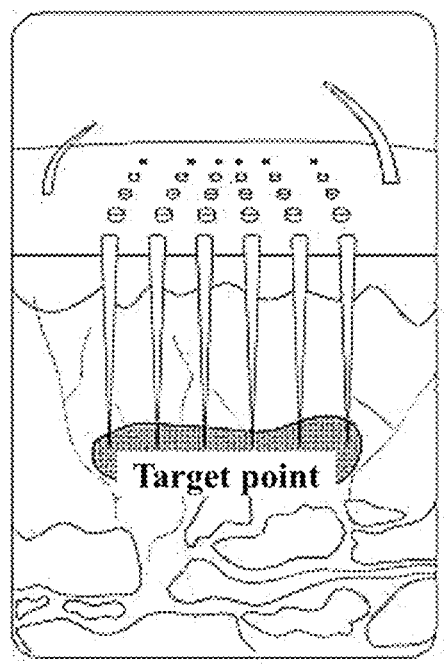
Figure 2:
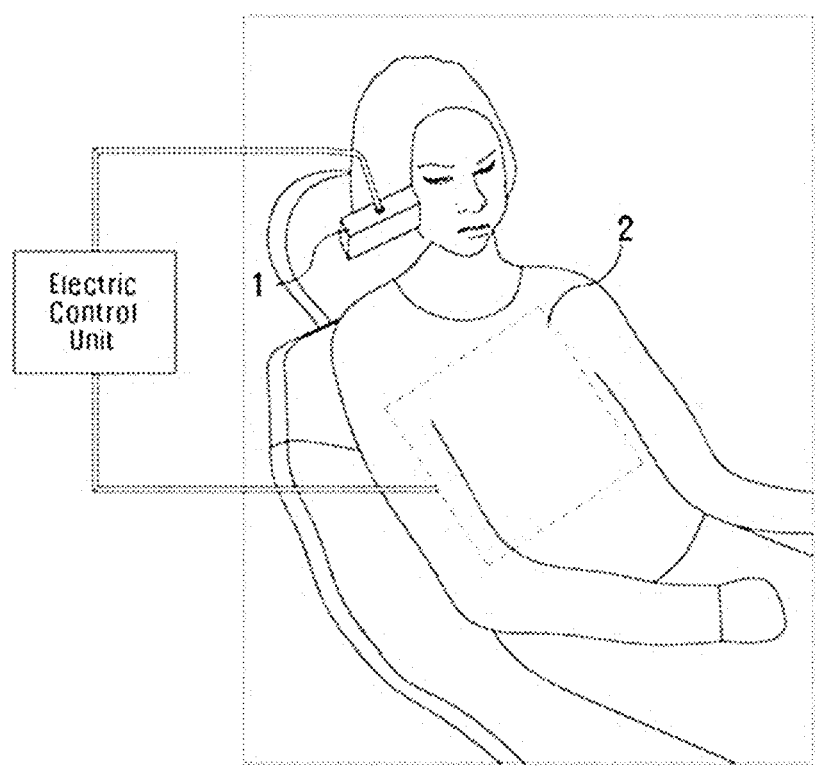
FIG. 2 is a view conceptually illustrating a target using a conventional skin treatment apparatus.

Advantage points and features of the inventive concept and a method of accomplishing thereof will become apparent from the following description with reference to the following figures, wherein embodiments will be described in detail with reference to the accompanying drawings. However, the inventive concept may be embodied in various different forms, and should not be construed as being limited only to the illustrated embodiments. Rather, these embodiments are provided as examples so that the inventive concept will be thorough and complete, and will allow those skilled in the art to fully understand the scope of the inventive concept. The inventive concept may be defined by scope of the claims.

The terminology used herein is provided for explaining embodiments, but the inventive concept is not limited thereto. Herein, singular terms are intended to include plural forms as well, unless the context clearly indicates otherwise. Furthermore, it will be further understood that the terms "comprises", "comprising," "includes" and/or "including", when used herein, specify the presence of stated components, but do not preclude the presence or addition of one or more other components. The same reference numerals will be assigned to the same component throughout the whole specification, and "and/or" refers to that components described include not only individual components, but at least one combination of the components. It will be understood that, although the terms "first", "second", etc., may be used herein to describe various components, these components should not be limited by these terms. These terms are only used to distinguish one component from another component. Thus, a first component to be described below may be a second component without departing from the teachings of the inventive concept.

Unless otherwise defined, all terms (including technical and scientific terms) used herein have the same meaning as commonly understood by those skilled in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "below", "beneath", "lower", "above", "upper", and the like, may be used herein to make it easier to describe the relationship between one component and another component. It will be understood that the spatially relative terms are intended to encompass different orientations of the device in use or operation in addition to the orientation depicted in the figures. For example, when a device illustrated in accompanying drawings is reversed, a device provided 'below' or 'beneath' another device may be placed 'above' another device. Accordingly, the term "below" may include both concepts of "below" and "above". A device may be oriented in a different direction. Accordingly, terminology having relatively spatial concepts may be variously interpreted depending on orientations.

Figure 5:
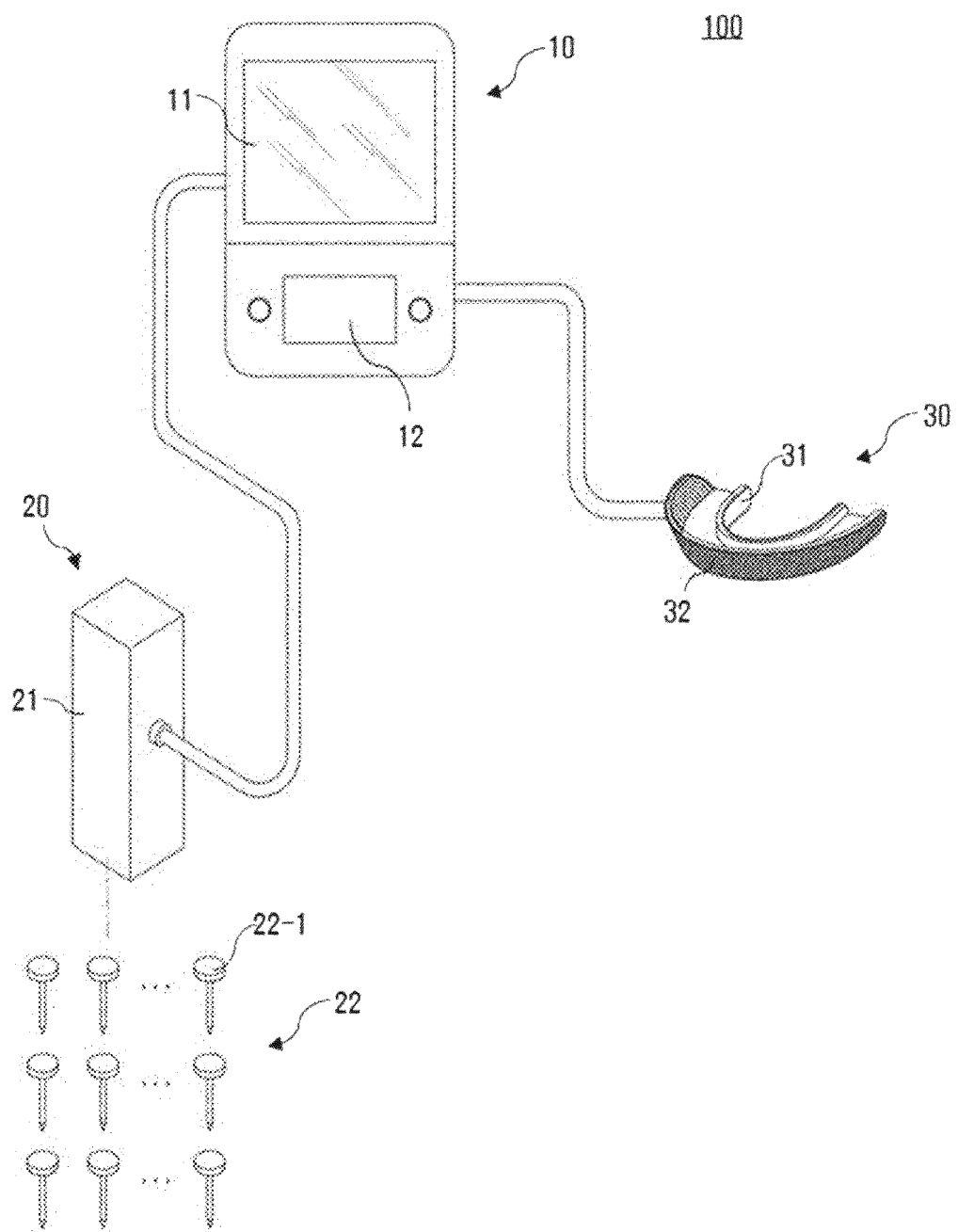
FIG. 5 is a view conceptually illustrating a skin treatment apparatus, according to the inventive concept.
Figure 6A:
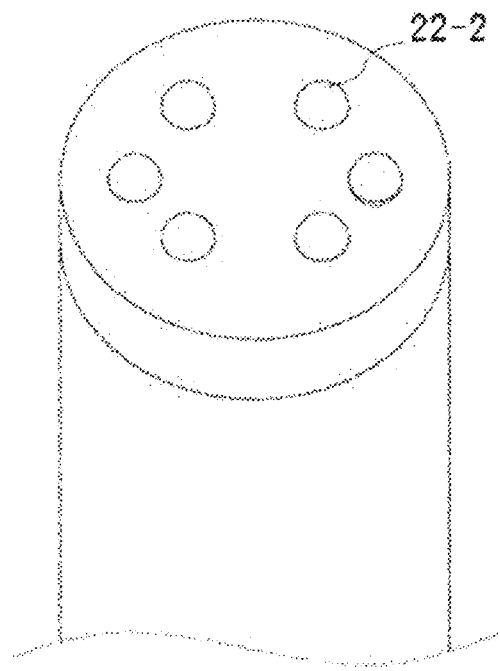
FIGS. 6A and 6B are views conceptually illustrating a power electrode unit, according to various embodiments of the inventive concept.
Figure 6B:
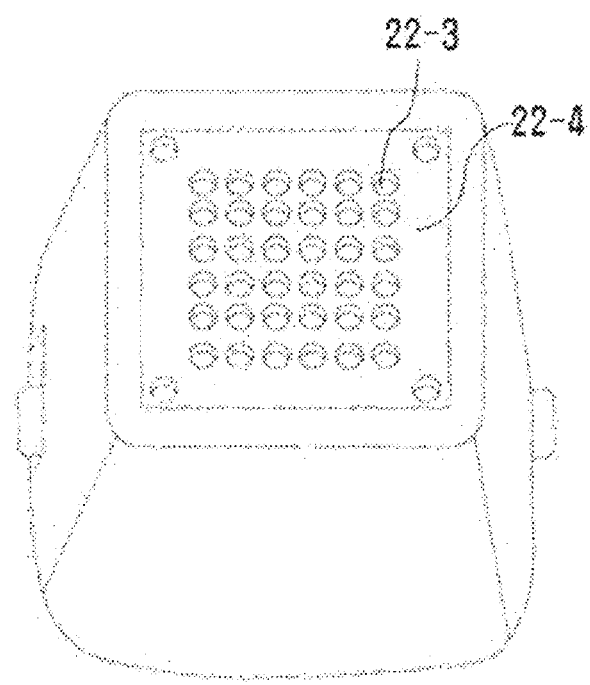
Figure 7:
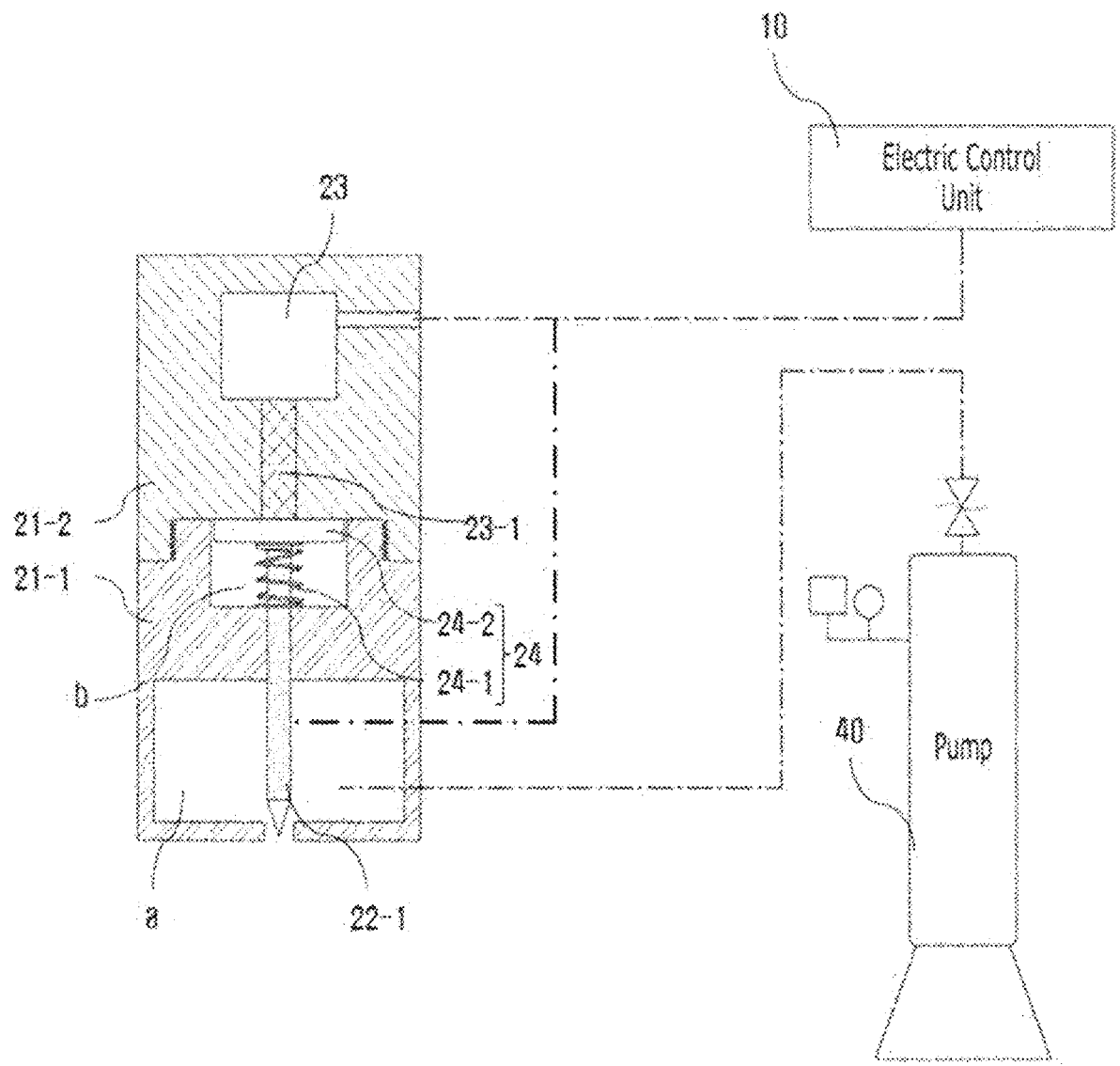
FIG. 7 is a view conceptually illustrating the sectional surface and the system of a hand piece, according to the inventive concept.
Figure 8:
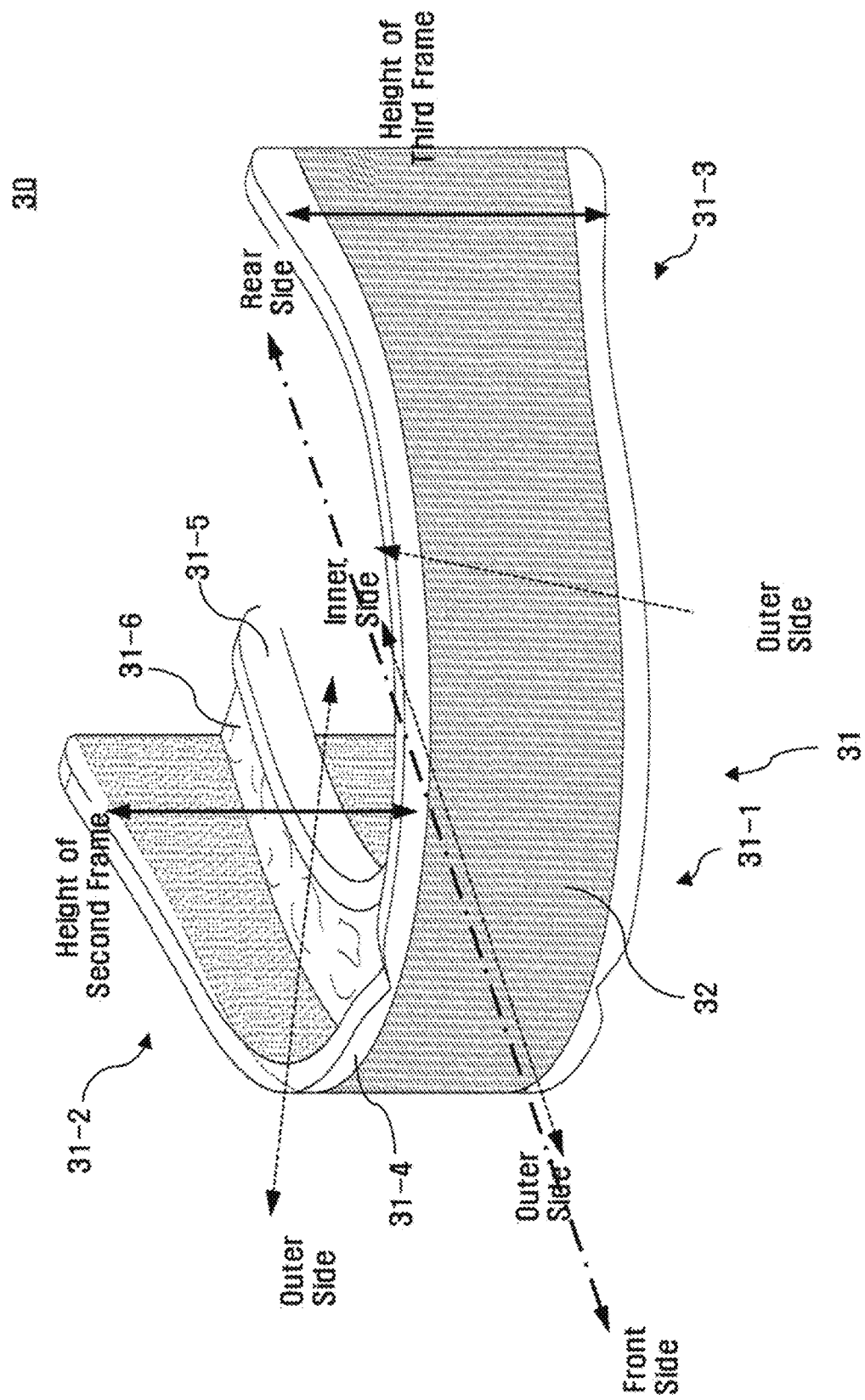
FIG. 8 is a perspective view illustrating a mouthpiece, according to the inventive concept.
Figure 9:
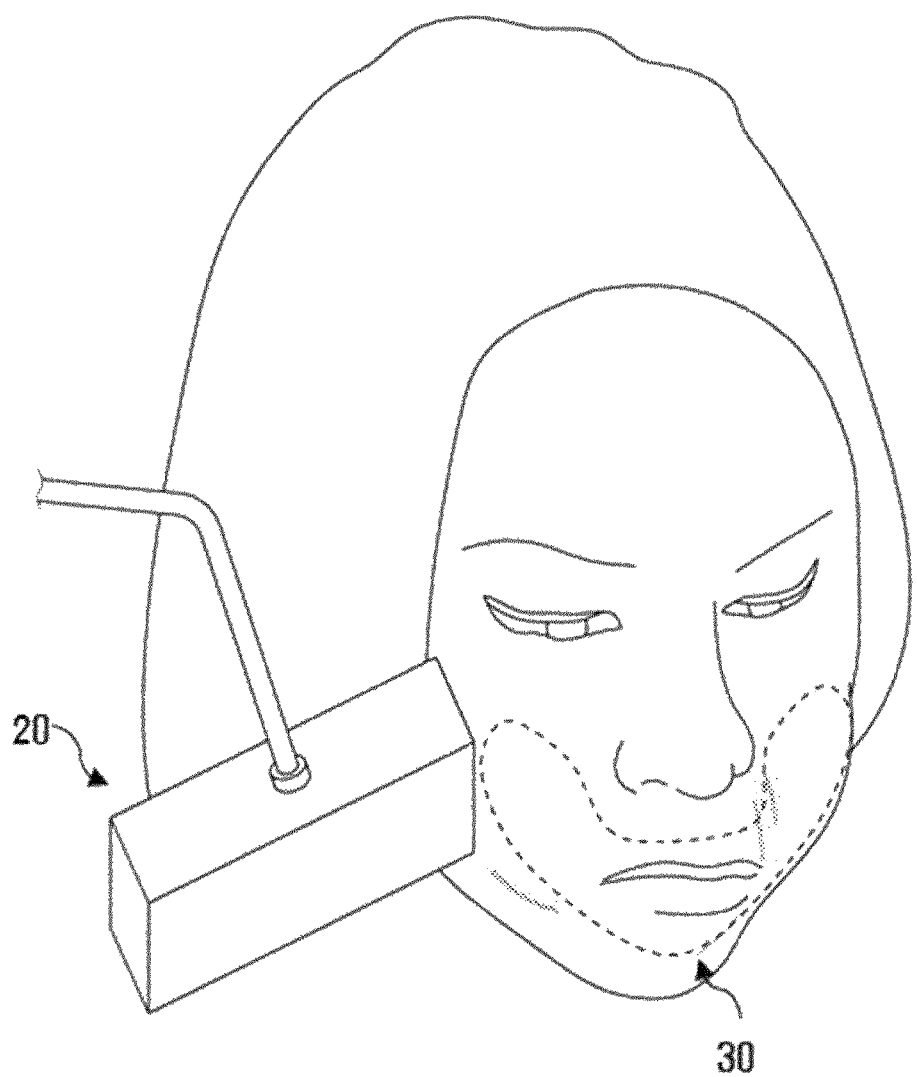
FIG. 9 is a view conceptually illustrating that a recipient is treated by using a handpiece and a mouthpiece, according to the inventive concept.

Hereinafter, an apparatus (hereinafter, referred to as "skin treatment apparatus") 100 for skin treatment according to the inventive concept will be described with reference to accompanying drawings. FIG. 5 is a view conceptually illustrating a skin treatment apparatus, according to the inventive concept, FIGS. 6A and 6B are views conceptually illustrating a power electrode unit, according to various embodiments of the inventive concept, FIG. 7 is a view conceptually illustrating the sectional surface and the system of a hand piece, according to the inventive concept, FIG. 8 is a perspective view illustrating a mouthpiece, according to the inventive concept, and FIG. 9 is a view conceptually illustrating that a recipient is treated by using a handpiece and a mouthpiece, according to the inventive concept.

According to the inventive concept, the skin treatment apparatus 100 may include an electric control unit 10, a handpiece 20, and a mouthpiece 30. In addition, according to the inventive concept, the skin treatment apparatus 100 may further include a pump 40 to inject cooling water or a chemical liquid into the handpiece 20.

The electric control unit 10 may electronically control devices constituting the skin treatment apparatus 100. To this end, the electric control unit 10 may be electrically connected to the handpiece 20 and the mouthpiece 30. The electric control unit 10 may control an intensity, wavelength, or direction of an AC current in a high frequency wavelength band, which is applied to a power electrode unit 22 of the handpiece 20.

The electric control unit 10 may include a display panel 11. Therefore, a doctor may receive various pieces of information necessary for skin treatment. For example, the display panel 11 may display an intensity, wavelength, or direction of the AC current in the high frequency wavelength band, which is currently applied. In addition, the display panel 11 may display biometrics information on a deep part of a skin tissue.

The electric control unit 10 may include an operating panel 12. Therefore, a doctor may select various modes necessary for skin treatment. The operating panel 12 may be provided in the form of a touchscreen. For example, the doctor may adjust the intensity of electrical energy applied to a skin of a recipient by clicking a button or an icon of the operating panel 12.

The handpiece 20, which is gripped in the hand of the doctor, may make contact with the skin of a patient. In this case, the handpiece 20 may generate electrical energy, as AC power is applied to the handpiece 20. As the electrical energy is generated between the handpiece 20 and the mouthpiece 30, heat is concentrated on the deep part of the skin such that skin treatment is performed. The handpiece 20 may include a housing 21, the power electrode unit 22, a driving unit 23, and a support unit 24.

The housing 21 may be an outer member to form an outer appearance of the handpiece 20. The housing 21 may be manufactured through plastic injection molding. However, the inventive concept is not limited thereto, but the housing 21 may be formed of various materials. The power electrode unit 22, the driving unit 23, and the support unit 24 may be disposed in the housing 21. In this case, the power electrode unit 22 may be supported by the support unit 24 to be moved in a longitudinal direction (vertical direction).

The housing 21 may include a first housing 21-1 and a second housing 21-2. The first housing 21-1 may be disposed at a lower portion of the housing 21, and the second housing 21-2 may be disposed at an upper portion of the housing 21. The first housing 21-1 and the second housing 21-2 may be screwed with each other.

The power electrode unit 22 and the support unit 24 may be disposed in the first housing 21-1. To this end, a first chamber "a" and a second chamber "b" may be formed inside the first housing 21-1. The first chamber "a" may be disposed at a lower portion of the first housing 21-1 and may be connected to an outside through a plurality of holes (openings) formed in the bottom surface of the first housing 21-1. The second chamber "b" may be disposed at an upper portion of the first housing 21-1. Meanwhile, the second chamber "b" may have an open part formed in a top surface thereof, and the open part of the second chamber "b" may be closed by a bottom surface of the second housing 21-2.

The power electrode unit 22 may be disposed in the first chamber "a" of the first housing 21-1, and the support unit 24 may be disposed in the second chamber "b" of the first housing 21-1. When the power electrode unit 22 moves down, the power electrode unit 22 may be exposed to the outside through the plurality of openings formed in the bottom surface of the first housing 21-1. Meanwhile, the upper portion of the power electrode unit 22 may be disposed in the second chamber "b" and supported by the support unit 24.

Meanwhile, according to the inventive concept, when the pump 400 is added to the skin treatment apparatus 100, various types of fluid may be injected into the first chamber "a". For example, the cooling water and the chemical liquid may be injected into the first chamber "a" to alleviate skin rash and pyrexy The driving unit 23 may be disposed inside the second housing 21-2. In this case, the driving unit 23 is connected to the support unit 24 at the boundary between the first housing 21-1 and the second housing 21-2 to drive the power electrode unit 22.

The power electrode unit 22 may be a "power terminal" to apply an AC current in a high frequency band. To this end, the power electrode unit 22 and a ground electrode unit 32 may be electrically connected to a power source (not illustrated) of the electric control unit 10.

According to the skin treatment apparatus 100 of the inventive concept, high-frequency wavelength band electrical energy having a higher energy density is applied to the damaged collagen and the aged skin tissue to heat the damaged collagen and the aged skin tissue with the higher-temperature heat, thereby improving a treatment effect (skin repair efficiency).

The current applied from the power electrode unit 22 may be refluxed from the ground electrode unit 32 to be described later. In other words, the power electrode unit 22 and the ground electrode unit 32 may electrically interact with each other such that an AC current in a high frequency wavelength band flows.

The power electrode unit 22 may include a plurality of needle electrodes 22-1. In this case, the power electrode unit 22 may be referred to as "RF needle electrode unit". Although the following description is made regarding the power electrode unit 22 including the plurality of needle electrodes 22-1 by way of example, the power electrode unit 22 according to the inventive concept is not limited thereto.

For example, as illustrated in FIG. 6A, the power electrode unit 22 may include a plurality of ball electrodes 22-2. In this case, the plurality of ball electrodes 22-2 may be rolled on the skin surface. In addition, since the plurality of ball electrodes 22-2 do not need to be driven in the vertical direction, the driving unit 23 may be omitted.

For example, as illustrated in FIG. 6B, the power electrode unit 22 may include a plurality of flat electrodes 22-3 having a pattern. In this case, an insulating layer 22-4, which is open in the above pattern part, may be stacked on the flat electrode 22-3 to form the pattern. In addition, since the flat electrode 22-3 does not need to be driven in the vertical direction, the driving unit 23 may be omitted.

The power electrode unit 22 may be disposed to be movable in the longitudinal direction (vertical direction) inside the housing 21. To this end, an upper end portion of the power electrode unit 22 is connected to a support pad 24-2 of the support unit 24 and elastically supported in the longitudinal direction (vertical direction). A lower end portion of the power electrode unit 22 may be a tip to penetrate the epidermal layer of a skin. Accordingly, when the power electrode unit 22 moves down, electrical energy may be applied to the dermal layer of the deep part of the skin. The depth of the deep part of the skin, to which the electrical energy is applied, may be determined by the stroke of the power electrode unit 22. The power electrode unit 22 may move up and be returned after applying electrical energy to the dermal layer of the deep part of the skin.

Each of the plurality of needle electrodes 22-1 may have the form of a needle extending in the vertical direction to form a length. A lower end portion of each of the plurality of needle electrodes 22-1 may be a tip.

The plurality of needle electrodes 22-1 may be arranged to form rows and columns on a plane perpendicular to the longitudinal direction (see FIG. 5). Therefore, the plurality of needle electrodes 22-1 may uniformly cover a wide range.

The driving unit 23 may drive the power electrode unit 22 in the longitudinal direction (vertical direction). Various types of devices may be used for the driving unit 23. For example, the driving unit 23 may be a "step motor". However, the inventive concept is not limited thereto. For example, the driving unit 23 may be a "hydraulic or pneumatic cylinder".

The driving unit 23 may include a rod 23-1. The rod 23-1 may be connected to the support pad 24-2 of the support unit 24, and may transmit vertical driving force, which is generated from the driving unit 23, to the support pad 24-2.

The support unit 24 may elastically support the power electrode unit 22 in the vertical direction. In addition, the support unit 24 may operate the power electrode unit 22 by receiving the driving force of the driving unit 23. The support unit 24 may include an elastic member 24-1 and the support pad 24-2.

The elastic member 24-1 of the support unit 24 may be a "helical spring". An upper end portion of the elastic member 24-1 is in contact with the support pad 24-2, and a lower end portion of the elastic member 24-1 is in contact with the bottom surface of the second chamber "b" of the first housing 22-1. Accordingly, the elastic member 24-1 may elastically support the support pad 24-2 in the vertical direction. Meanwhile, as described above, the support pad 24-2 is connected (coupled) to the upper end portion of the power electrode unit 22. Accordingly, the power electrode unit 22 may be elastically supported by the support unit 24 in the vertical direction.

The mouthpiece 30 may be inserted into the oral cavity of the patient. The AC power in the high frequency wavelength band of the handpiece 20 may be transmitted to the mouthpiece 30 through the deep part of the skin. The mouthpiece 30 may include a frame 31 and the ground electrode unit 32.

The frame 31 may be an outer member to form an outer appearance of the mouthpiece 30. The frame 31 may be formed of a non-conductive material (for example, synthetic resin such as rubber or plastic). This is to prevent high-frequency electrical energy from being conducted through a dental implant of a recipient.

The frame 31 may include a first frame 31-1, a second frame 31-2, and a third frame 31-3. The first frame 31-1, the second frame 31-2, and the third frame 31-3 may be integrally formed.

The first frame 31-1 may have a shape substantially extending from left to right based on the recipient (wearer), and may have a curvature formed at the front portion thereof. At least one front tooth may be disposed in the first frame 31-1. In other words, a tooth, which is disposed in front of a plurality of teeth, may be seated in the first frame 31-1.

The second frame 31-2 may have a shape substantially extending rearward from one end (right end) portion of the first frame 31-1. At least one right molar may be placed on the second frame 31-2. In other words, a tooth, which is disposed at the right, of the plurality of teeth may be seated on the second frame 31-2.

The third frame 31-3 may have a shape substantially extending rearward from an opposite end (left end) portion of the first frame 31-1. At least one left molar may be disposed in the third frame 31-3. In other words, a tooth, which is disposed at the left side, the plurality of teeth, may be seated on the second frame 31-3.

A larger area having a height substantially more increased rearward may be formed in at least a portion of the second frame 31-2 and the third frame 31-3. Accordingly, the treatment may proceed while maintaining the facial skin in a tightly spread state.

At least one of the first frame 31-1, the second frame 31-2, and the third frame 31-3 may include a first cover 31-4 disposed at an outer side, a second cover 31-5 disposed at an inner side, and a seating part 31-6 interposed between the first cover 31-4 and the second cover 31-5.

In other words, the first cover 31-4 of the first frame 31-1 may be disposed in front of the second cover 31-5 of the first frame 31-1, the first cover 31-4 of the second frame 31-2 may be disposed on the right side of the second cover 31-5 of the second frame 31-2, and the first cover 31-4 of the third frame 31-3 may be disposed to the left side of the second cover 31-5 of the third frame 31-3.

The first cover 31-4 and the second cover 31-5 may surround the outer and inner surfaces of the plurality of teeth. As the seating part 31-6 is interposed between the first cover 31-4 and the second cover 31-5, the seating part 31-6 may be stuck between a plurality of upper teeth and a plurality of lower teeth. The plurality of upper teeth and the plurality of lower teeth may be stably fixed by the seating part 31-6. To this end, an intaglio groove corresponding to the tooth shape of a wearer may be formed in the seating part 31-6.

The ground electrode unit 32 may be a "ground terminal" through which an AC current in a high frequency wavelength band transmitted to the skin is refluxed. In other words, the ground electrode unit 32 may perform electromagnetic interaction with the power electrode unit 22 such that an AC current in a high frequency wavelength band flows. To this end, the ground electrode unit 32 may be electrically connected to a power supply (not illustrated) of the electric control unit 10.

Meanwhile, the ground electrode unit 32 may be integrally formed with the first frame 31-1, the second frame 31-2, and the third frame 31-3 while continuously extending, to prevent the AC current, which is generated through the electrical interaction with the power electrode unit 22, from being concentrated on a specific fine part of a facial surface of the wearer (since the skin treatment apparatus according to the inventive concept uses high-frequency energy, the user may be scalded or feel pain when the electrical energy is concentrated).

When the ground electrode unit 32 is inserted into an oral cavity, the ground electrode unit 32 may be disposed in at least a portion between a lip and at least one front tooth, at least a portion between a right cheek mucosa and at least one right molar, and a portion between a left cheek mucosa and at least one left molar.

In other words, the ground electrode unit 32 may be integrally formed at a larger part in a mouth and may be continuously distributed. Therefore, according to the skin treatment apparatus 100 of the inventive concept, the electric energy may be prevented from being concentrated on a specific fine area.

Meanwhile, the ground electrode unit 32 is disposed as close to the power electrode unit 22 as possible for the electrical interaction. To this end, the ground electrode unit 32 may be disposed on an outer side surface of the frame 31 or may constitute the outer side surface of the frame 31. In other words, the ground electrode unit 32 may be disposed on the outer side surface of the first cover 31-4 or the outer side surface of the first cover 31-4.

Meanwhile, the ground electrode unit 32 may be disposed on an intermediate portion of the outer side surface of the first cover 31-4 or may constitute the intermediate portion of the outer side of the first cover 31-4 such that an upper portion and a lower portion of the outer side surface of the first cover 31-4 are exposed to the outside. In other words, the height of the first cover 31-4 may be higher than the height of the ground electrode unit 32, and upper and lower portions of the first cover 31-4 may not overlap with the ground electrode unit 32.

The position of a dental implant of the wearer is prevented from being overlapped with the ground electrode unit 32, thereby preventing high-frequency electrical energy from being conducted to the dental implant.

Figure 3:
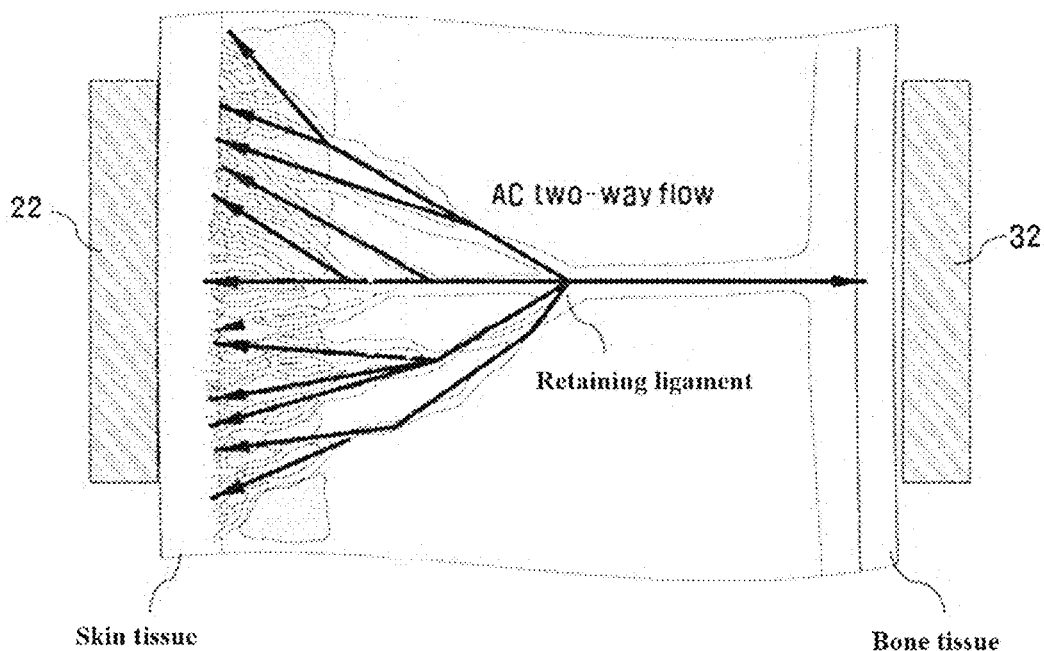
FIG. 3 is a view conceptually illustrating that an AC current flows through a retaining ligament of a facial surface, when skin treatment is performed using a skin treatment apparatus, according to the inventive concept.
Figure 4:
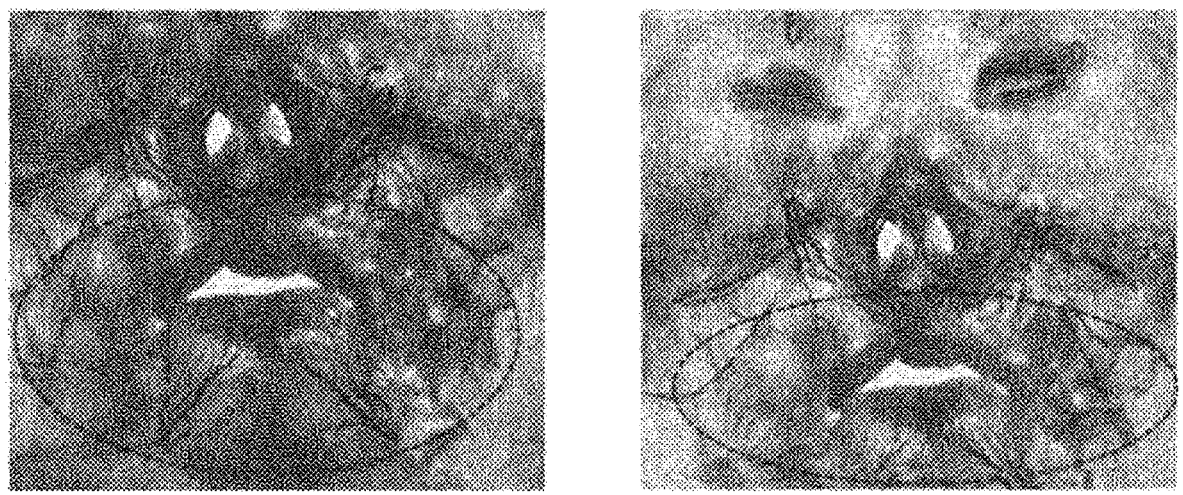
FIG. 4 is a view illustrating the concept that internal mucous membranes and nerves are distributed in a planar shape while forming mesh network when viewed from the inside of a facial surface of a human body.

Meanwhile, the ground electrode unit 32 may cover at least 95% of the outer side surface of the first cover 31-4. The area of the ground electrode unit 32 is expanded, thereby covering all retaining ligaments, blood vessels, and intercellular fibrous tissues illustrated in FIGS. 3 and 4.

According to the skin treatment apparatus of the inventive concept, the power electrode unit is displaced on the outer side (epidermis) while interposing the facial skin between the outer side and teeth, and the ground electrode unit is disposed in the inner side (the inside of an oral cavity) such that the power electrode unit and the ground electrode unit are adjacent to each other. Accordingly, the higher electrical energy efficiency may be exhibited. In addition, the current may easily flow through the retaining ligament and the blood vessel, and the intercellular fibrous tissue. Accordingly, the retaining ligament and a blood vessel, and the deep part of the intercellular fibrous tissue may be utilized as the electricity passage.

Furthermore, since the AC current flows between the power electrode unit and the ground electrode unit while changing directions depending on the cycle. Accordingly, when the AC current flows from the inner side to the outer side, the AC current flows along several strands split from the central strand of the retaining ligament, so the electric path extending from the deep part of the skin is made (see FIG. 3).

Therefore, according to the skin treatment apparatus of the inventive concept, the retaining ligament and the blood vessel, and the intercellular fibrous tissue are utilized as the electricity passage, thereby effectively improving the sagging of the facial surface caused as the skin is aged.

In addition, according to the skin treatment apparatus of the inventive concept, the electrical energy in the high frequency wavelength band is used to employ the high-density electrical energy. As the electrical energy in the high frequency wavelength band is used, heat is intensively applied to a part, which has the power electrode unit, of the skin of the recipient, so the recipient may be scalded or feel pain.

To solve the problem, according to the mouthpiece of the skin treatment of the inventive concept, the ground electrode unit is integrally formed on the outer surface of the frame while continuously extending along the outer side of the frame, such that the electrical energy generated from the part having the power electrode unit is dispersed, thereby preventing heat from being intensively applied to the heating part (if the ground electrode unit is intermittently formed with a plurality of unit electrodes spaced apart from each other, only the unit electrode at a part facing the power electrode unit is electrically activated, so the heating part may be concentrated at the part facing the power electrode unit).

Therefore, according to the skin treatment apparatus of the inventive concept, the treatment effect may be increased by using the high frequency wavelength band having the higher energy density and the heating part may be prevented from being concentrated, so the safety may be increased.

In addition, as the mouthpiece of the inventive concept is inserted into the oral cavity, the mucous membrane is also electrically stimulated to generate new fibrous tissues and elastic tissues, thereby increasing tension and elasticity of the internal mucosa. Thus, since the treatment proceeds with respect to the facial skin (facial tightening and tenting) maintained tightly spread, the power electrode unit precisely makes contact with the target point, and the electrical energy is efficiently transmitted, thereby increasing the treatment effect. Furthermore, the upper structure of the sagged upper portion inside the oral cavity is tensioned, thereby improving the outer appearance of the aged skin.

The effects of the inventive concept are not limited to the above, but other effects, which are not mentioned, will be apparently understood to those skilled in the art.

Although embodiments of the inventive concept have been described with reference to accompanying drawings, those skilled in the art should understand that various modifications are possible without departing from the technical scope of the inventive concept or without changing the technical sprite or the subject matter of the inventive concept. Therefore, those skilled in the art should understand that the technical embodiments are provided for the illustrative purpose in all aspects and the inventive concept is not limited thereto.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A mouthpiece for skin treatment, the mouthpiece comprising:
   a frame; and
   a ground electrode unit on the frame,
   wherein the frame includes:
   a first frame disposed in front;
   a second frame extending rearward from one end portion of the first frame; and
   a third frame extending rearward from an opposite end portion of the first frame, and
   wherein the ground electrode unit is integrally formed with the first frame, the second frame, and the third frame while continuously extending,
   wherein at least one of the first frame, the second frame, and the third frame may include a first cover disposed at an outer side, a second cover disposed at an inner side, and a seating part interposed between the first cover and the second cover,
   wherein the ground electrode unit is disposed on at least a portion of an outer side surface of the first cover or constitutes the at least a portion of the outer side surface of the first cover, and wherein the ground electrode unit covers at least 95% of the outer side surface of the first cover.

2. The mouthpiece of claim 1, wherein at least one front tooth is configured to be placed on the first frame, at least one right molar is configured to be placed on the second frame, and at least one left molar is configured to be placed on the third frame, when the frame is inserted into a mouth.

3. The mouthpiece of claim 1, wherein the ground electrode unit is configured to be positioned in at least a portion between a lip and at least one front tooth, at least a portion between a right cheek mucosa and at least one right molar, and a portion between a left cheek mucosa and at least one left molar, when being inserted into a mouth.

4. The mouthpiece of claim 1, wherein a front portion of the first frame has a curvature, and
wherein at least a portion of the second frame and the third frame has an area part having a height increased toward a rear portion compared to the front portion.

5. The mouthpiece of claim 1, wherein the frame includes a non-conductive material, and the ground electrode unit is configured to be positioned on an intermediate portion of the outer side surface of the first cover or configured to constitute the intermediate portion of the outer side surface of the first cover such that an upper portion and a lower portion of the outer side surface of the first cover are exposed to an outside of the mouthpiece, and
wherein the seating part is configured to be stuck between a plurality of upper teeth and a plurality of lower teeth, when the seating part is inserted into a mouth.

6. The mouthpiece of claim 1, wherein an intaglio groove having a shape corresponding to a tooth shape of a wearer is formed in the seating part.

7. An apparatus for skin treatment, the apparatus comprising:
an electric control unit;
a mouthpiece for skin treatment according to claim 1, which is electrically connected to the electric control unit; and
a handpiece electrically connected to the electric control unit, and comprising
an external power electrode unit that is configured to receive power from the electric control unit and to electrically interact with the ground electrode unit of the mouthpiece for the skin treatment such that an AC current in a high frequency wavelength band flows.

* * * * *